United States Patent [19]

Weisman et al.

[11] Patent Number: 6,090,409

[45] Date of Patent: Jul. 18, 2000

[54] THERAPEUTIC USES OF FINASTERIDE

[76] Inventors: Kenneth M. Weisman, 30 Springton Point Dr., Newtown Square, Pa. 19073; Michael Goldberg, 20 Aspen Dr., Ivyland, Pa. 18974

[21] Appl. No.: 09/042,273

[22] Filed: Mar. 13, 1998

Related U.S. Application Data

[60] Provisional application No. 60/041,070, Mar. 18, 1997.

[51] Int. Cl.⁷ ....................................................... A61K 9/20
[52] U.S. Cl. ............................ 424/464; 424/455; 424/489
[58] Field of Search .................................... 424/464, 489; 514/176

[56] References Cited

U.S. PATENT DOCUMENTS 5,175,155  12/1992  Juniewicz et al. ...................... 514/176

*Primary Examiner*—Thurman K. Page
*Assistant Examiner*—William Benston
*Attorney, Agent, or Firm*—Caesar, Rivise, Bernstein, Cohen & Pokotilow, Ltd.

[57] ABSTRACT

The method of decreasing atherosclerosis and its complications, such as, myocardial infarction, stroke and peripheral vascular disease involving administering to a human or animal an amount of finasteride sufficient to decrease atherosclerosis and its complications.

3 Claims, No Drawings

THERAPEUTIC USES OF FINASTERIDE

This application claims the benefit of the filing date of Mar. 18, 1997 of Provisional patent application Ser. No. 60/041,070.

BACKGROUND OF THE INVENTION

Finasteride, a synthetic 4-azasteroid compound. 4-azaandrost-1-ene-17-carboxamide, N-(1,1-dimethylethyl)-3-oxo-(5a 17B)-, sold under the trade name Proscar, as identified by U.S. Pat. No. 5,175,155, the entire disclosure is incorporated by reference herein, is known for use in treatment of benign prostatic hypertrophy (BPH). Said U.S. Pat. No. 5, 175,155 discloses the combination of finasteride and another agent, but preferably in the present invention finasteride is the only active ingredient, although combinations with other active ingredients are contemplated.

The present invention involves the use of finasteride in the prevention and treatment of atherosclerosis, coronary artery heart disease, stroke, and peripheral vascular disease in humans and animals.

It was observed that patients to whom finasteride was being administered for treatment of benign prostatic hypertrophy seemed to have a lower incidence of atherosclerosis and heart disease.

Finasteride was being administered at a dosage of a single oral 5 mg tablet a day. This is the same tablet used in treatment of BPH as disclosed in U.S. Pat. No. 5,175,155 and such dosage applies in the present invention. However, use of a 2 mg or 10 mg oral tablet is contemplated.

Two studies were undertaken to determine whether finasteride was, in fact, effective in lessening the incidence of heart disease and other complications of atherosclerosis.

The result of the first study is as follows; A list of patients diagnosed with benign prostatic hypertrophy in late 1992 and 1993 was located. Treatment had been initiated with either finasteride or another oral agent of a different class (alpha-blocker). Patients were then contacted and an interval history was taken. In the control group of 45 subjects, 7 events (either cardiac bypass or heart attack) occurred in 6 subjects over 288 subject-years. In the finasteride treated group of 22 subjects there were no events over 61 subject-years. (Some patients had discontinued the use of finasteride, and only those on the drug for at least a year were considered.) We believe significantly more events occurred in the control group compared to the finasteride treated group. (95% Cl equal to 0.65% to 4.2%)

In the second study patients of the practice were given a questionnaire. Various patients had been treated with finasteride for varying lengths of time. Only those on the drug for at least one year were considered. The average time on finasteride was 3 years. The number of cardiac events occurring in the patients taking finasteride was only 4 events over 242 patient-years. (1.6%/yr.) In the control group 26 events occurred in the 3 years prior over 732 patient-years. (3.5%/yr.)

The 45% decrease observed in cardiac events is believed to be significant. (90% Cl equal to 1.4% to 3.7%)

It should be understood that this invention will apply to the administration of finasteride in any form for the purpose of systemic absorption for the purpose of treating, and preventing atherosclerosis and its complications including but not limited to myocardial infarction, stroke, and peripheral vascular disease. Such forms will include not only tablets, but also subcutaneous pellets or cutaneous patches or other forms resulting in systemic availability of the drug. The active ingredient can be administered as a liquid in the form of a solution or a dispersion using appropriate solvents and preservatives as well as adjusting the pH to the range of maximum stability.

In the formulation of either solid or liquid pharmaceutically acceptable inactive ingredients may be used. These include excipients, preservatives or flavorings.

Methods of manufacturing finasteride are disclosed in U.S. Pat. Nos. 4,760,071 and 5,468,860.

Without further elaboration the foregoing will so fully illustrate our invention that others may, by applying current and future knowledge, adopt the same for use under various conditions of service.

We claim:

1. A method of decreasing atherosclerosis and its complications not limited to myocardial infarction, stroke and peripheral vascular disease comprising administering to a human or an animal an amount of finasteride sufficient to decrease atherosclerosis and its complications.

2. The method of claim 1 wherein the effective amount of finasteride is present in a 5 mg solid oral tablet.

3. The method of claim 1 wherein finasteride is administered as a part of a liquid solution or dispersion, or patch, subcutaneous pellet or any other method with the intent of accomplishing systemic absorption of the drug.

* * * * *